(12) United States Patent
Dykaar

(10) Patent No.: US 10,436,967 B2
(45) Date of Patent: Oct. 8, 2019

(54) OPTICAL DIFFUSER

(71) Applicant: Douglas Raymond Dykaar, Waterloo (CA)

(72) Inventor: Douglas Raymond Dykaar, Waterloo (CA)

( * ) Notice: Subject to any disclaimer, the term of this patent is extended or adjusted under 35 U.S.C. 154(b) by 117 days.

(21) Appl. No.: 15/300,195

(22) PCT Filed: Apr. 3, 2015

(86) PCT No.: PCT/US2015/024314
§ 371 (c)(1),
(2) Date: Sep. 28, 2016

(87) PCT Pub. No.: WO2015/154011
PCT Pub. Date: Oct. 8, 2015

(65) Prior Publication Data
US 2017/0184772 A1    Jun. 29, 2017

Related U.S. Application Data

(60) Provisional application No. 61/975,357, filed on Apr. 4, 2014.

(51) Int. Cl.
| | | |
|---|---|---|
| *G02B 6/32* | (2006.01) | |
| *F21V 8/00* | (2006.01) | |
| *G02B 6/26* | (2006.01) | |
| *G02B 5/02* | (2006.01) | |
| *A61N 5/06* | (2006.01) | |
| *A61B 18/22* | (2006.01) | |

(52) U.S. Cl.
CPC ......... *G02B 6/0008* (2013.01); *G02B 5/0221* (2013.01); *G02B 5/0242* (2013.01); *G02B 6/262* (2013.01); *A61B 2018/2261* (2013.01); *A61N 5/062* (2013.01); *A61N 2005/063* (2013.01)

(58) Field of Classification Search
CPC ....................................................... G02B 6/262
USPC ......................................................... 385/123
See application file for complete search history.

(56) References Cited

U.S. PATENT DOCUMENTS

| | | | |
|---|---|---|---|
| 5,074,632 A | 12/1991 | Potter | |
| 5,263,103 A | 11/1993 | Kosinski | |
| 5,536,265 A * | 7/1996 | van den Bergh | A61B 18/22 606/15 |
| 5,751,869 A | 5/1998 | Li et al. | |
| 5,946,441 A | 8/1999 | Esch | |

(Continued)

FOREIGN PATENT DOCUMENTS

| | | |
|---|---|---|
| EP | 0 676 218 A1 | 10/1995 |
| GB | 2 227 333 A | 7/1990 |

OTHER PUBLICATIONS

"International Search Report for PCTUS2015/024314 dated Jul. 7, 2015".

(Continued)

*Primary Examiner* — Eric Wong
(74) *Attorney, Agent, or Firm* — Nyssa Inc.

(57) ABSTRACT

A device includes an optical delivery fiber having a core having a first inside diameter joined to a capillary having an outer surface and a capillary tube having an inner surface. The capillary tube has a second inside diameter in the region of the joining to the optical delivery fiber. The second inside diameter is less than the first inside diameter of the delivery fiber.

20 Claims, 3 Drawing Sheets

(56) References Cited

U.S. PATENT DOCUMENTS

| | | | |
|---|---|---|---|
| 6,004,315 A | 12/1999 | Dumont | |
| 6,091,490 A | 7/2000 | Stellman et al. | |
| 6,398,778 B1 | 6/2002 | Chi-Hung | |
| 9,090,666 B2 * | 7/2015 | Wang | C07K 1/26 |
| 2001/0056278 A1 * | 12/2001 | Nield | A61B 18/22 |
| | | | 606/15 |
| 2005/0244101 A1 * | 11/2005 | Kitabayashi | G02B 6/262 |
| | | | 385/33 |
| 2008/0065058 A1 | 3/2008 | Neuberger | |
| 2010/0016845 A1 * | 1/2010 | Hanley | A61B 18/24 |
| | | | 606/15 |
| 2010/0232745 A1 | 9/2010 | Stacey | |
| 2010/0278486 A1 * | 11/2010 | Holland | G02B 6/262 |
| | | | 385/43 |
| 2011/0002584 A1 | 1/2011 | Griffin | |
| 2011/0085241 A1 | 4/2011 | Purchase et al. | |
| 2011/0212411 A1 | 9/2011 | Sinofsky | |
| 2013/0317295 A1 | 11/2013 | Morse | |

OTHER PUBLICATIONS

"Supplementary European Search Report dated Oct. 24, 2017 in connection with EP 15 77 4297".

\* cited by examiner

OPTICAL DIFFUSER

REFERENCE TO RELATED APPLICATIONS

This application claims the benefit of U.S. provisional application No. 61/975,357.

FIELD OF THE INVENTION

This invention relates to a new optical diffuser, where an optic fiber is coupled to a capillary tube. This optical diffuser has applications in the optical excitation of biological systems.

BACKGROUND

Optical diffusers are devices that scatter light. Optical diffusers can be used in conjunction with optical fiber to introduce scattered light into specific locations that are otherwise hard to reach.

Optical excitation of biological systems is an important application of this concept, and includes Photo-Dynamic Therapy (PDT) and opto-genetics. Many devices have been developed to accomplish this simple sounding task. These devices consist of an optical source, a delivery device, such as an optical fiber, and a device for coupling light out of the delivery fiber and into the biological system. The coupling device or diffuser is often complicated, expensive to produce, mechanically fragile, and cannot be easily redesigned for different applications.

In the case of PDT, optical excitation is typically in the visible red portion of the electromagnetic spectrum, requires Continuous Wave (CW) excitation, narrow bandwidth and high power (W). For PDT applications, it is desirable that the diffuser illuminates the surrounding region in a uniform, or Lambertian distribution. An optical diffuser suitable for PDT in one context may well be inappropriate for different applications.

An example of an FDA approved PDT drug is Photofrin™ or porfimer sodium for use against esophageal cancer and endobronchial cancer. The porfimer sodium is injected intravenously, and 40-50 hours after injection the area is illuminated with laser light. According to the product monograph, the laser system must be approved to deliver a stable power output at a wavelength of 630 plus/minus 3 nm. Light is delivered to the tumor by fiber optic diffusers passed through the operating channel of an endoscope/bronchoscope.

An optical diffuser designed to work with a specific light source and fiber optic cable to reliably deliver a 630 plus/minus 3 nm (i.e. to work with porfimer sodium) may be less effective or even ineffective when used with other PDT drugs.

Conventional optical diffusers use coreless optical fibers and/or bulk scattered elements.

For example, the use of coreless optical fiber for use as an optical termination or "beam dump" is described in U.S. Pat. No. 5,263,103 of Kosinski, "Low Reflection Optical Fiber Termination". In U.S. Pat. No. 5,263,103 a coreless optical fiber is fabricated in the standard way, with the single exception that the core is omitted. The index of the glass is chosen to match, or nearly match that of the core of the fiber it is to be spliced or otherwise mated to. The surface of the resulting splice or mating region can be recoated to produce a seamless splice between the two fiber types. Optically, the coreless fiber behaves as a lossy waveguide, which is the reason for its desirability as a termination device. The coreless fiber is used as a "beam dump", i.e. a fiber where light entering the coreless fiber produces essentially no reflected energy. A typical application would be as a dump for residual infra-red pump light in an Erbium doped optical amplifier.

Coreless fiber has also been used as end-caps for cored fiber, to allow high power beams to focus through the coreless fiber without exposing the core. The incoming beam presents a larger spot on the exposed coreless face, and hence a lower energy density, compared to focusing directly on an exposed core, thus avoiding optically induced damage.

For use as a diffuser, the loss per unit length of coreless fiber is low, so that for a high level of diffusion a length of many cm—typically greater than 10 cm—is required. In contrast, diffusers for use in PDT should be relatively short (as they are inserted into biological environments), typically 5 cm or less. To achieve desired scattering in a length of 5 cm or less, a coreless fiber would need to be modified to increase surface scattering, either by roughening the surface, by coating the surface with a material containing scattering particles, or by coating the surface with a plastic heat shrink tubing that scatters light, or by cutting threads into the glass.

Scattering can also be achieved through bulk scattering elements. For example, U.S. Pat. No. 5,074,632 discloses creating a cavity at the end of optical fiber and filling the cavity with a scattering material. U.S. Pat. No. 5,946,441 discloses coupling light out at a nose come attached to optical fiber, and also discloses abrading the surface of the nose-cone to increase scattering. Note that in doing so, the nose cone can be of greater diameter than the optic fiber, which is undesirable when used for PDT or other applications requiring insertion into biological systems.

Diffraction via gratings is disclosed in U.S. Pat. No. 6,398,778 in which Bragg gratings are formed in the distal end of the fiber to couple light out of the fiber. The gratings are typically formed using a planar mask, so the resulting grating couples light in a preferred direction. Multiple gratings can be fabricated to reduce the directionality but results in increased cost and reduced mechanical strength.

The use of chemical etching is disclosed in U.S. Pat. No. 6,004,315. To increase scattering from a diffuser made from conventional, glass-cored fiber, by the process disclosed in U.S. Pat. No. 6,004,315, the cladding must be removed. Cladding removal uses a preferential chemical etch process and requires careful implementation and results in a significantly weakened fiber.

In summary the prior art processes have various drawbacks: in some cases complications and expense in construction, in other cases inefficient scattering resulting in long lengths needed to achieve a desired scattering, and in other cases the diffuser is fragile, easy to break and difficult to maintain.

SUMMARY

The inventive device joins a capillary to the end of an optical delivery fiber. The inner diameter of the capillary tube is smaller than the inner diameter of the core of the optical delivery fiber. The introduction of the capillary tube forces the optical energy into an annulus shape. This mode requires very high order modes and propagates with high loss, where the losses result from light coupling out of the capillary. Various embodiments, as set out below, allow the type and efficiency of scattering to be adjusted. When the capillary is spliced to the end of an optical delivery fiber, the capillary tube may be partially or totally collapsed as part of the splicing process (for example through fusion splicing), ensuring a greater coupling efficiency into the capillary and propagation loss in the capillary.

This device addresses several of the drawbacks discussed above. This device is an efficient scatterer, and thus can be shorter (less than 10 cm or less than 5 cm in length); this is desirable when the diffuser is to be used in the optical excitation of biological systems such as tumors, and is particularly desirable in cases where an easily accessible opening such as the esophagus is not available. The capillary can be chosen to have an outer diameter than matches or is smaller than the optic fiber, which is also desirable for use with biological systems.

This device provides a simple, easily constructed, robust and scalable device for optical excitation of biological systems. If the distal end of the capillary tube is sealed, the device is easy to clean and maintain. The scattered light can be controlled in several methods as described below, allowing control of the output radiation.

It is generally desirable for biological applications to have a diffuser with close to 100% loss (i.e. with no back-reflection of the light), low absorption, and a small profile in terms of both length and diameter. Low absorption is desirable for biological applications since absorption generally results in heat, which is undesirable in biological applications. If the capillary used in the inventive device is glass or silica, then the inventive device has all these properties: high loss, low absorption, short length and a diameter at least as small as the optic fiber. The inventive diffuser is also simple to manufacture (albeit there are several embodiments that involve additional manufacturing steps), robust and easy to clean and maintain.

The diffuser can also be used as a sensor because of the low absorption. For example, in applications where the target fluoresces, light that is collected by the capillary will be coupled back into the delivery fiber. This light can detected by standard techniques such as time dependent gating (after delivery of an optical excitation pulse) or by using wavelength selective techniques if the florescence is at a different wavelength than the excitation.

In accordance with the present invention, there is provided a device comprising an optical delivery fiber having a core having a first inside diameter joined to a capillary having an outer surface and a capillary tube having an inner surface and a second inside diameter in the region of the joining to the optical delivery fiber, wherein the second inside diameter is less than the first inside diameter of the delivery fiber.

In another aspect of the present invention, the capillary is a glass or silica capillary. In another aspect of the present invention, the inner surface of the capillary tube is roughened or textured. In another aspect of the present invention, the capillary tube is filled with a material containing optically scattering particles. In another aspect of the present invention, the capillary tube is filled with a material containing fluorescent or other wavelength conversion material.

In another aspect of the present invention, the capillary tube is collapsed at two points. In yet another aspect of the present invention, the capillary tube is tapered in the region of the joining to the optical delivery fiber. In another aspect of the present invention, the capillary tube is collapsed in the region of the joining to the optical delivery fiber. In another aspect of the present invention, the capillary tube is sealed at a distal end of the diffuser. In yet another aspect of the present invention, a plurality of capillaries is joined to the optical delivery fiber.

In another aspect of the present invention, the capillary outer surface is roughened or textured. In another aspect, a density of roughening or texturing of the capillary outer surface is varied along the capillary. In yet another aspect of the invention, a density of roughening or texturing of the capillary outer surface is varied along the capillary to match a pre-determined light scattering condition.

In another aspect of the invention, the capillary is less than 5 cm long. In another aspect the capillary is approximately 1 cm long. In another aspect of the invention, the capillary tube has a non-circular cross-section. In another aspect of the invention, the capillary tube has a star-like cross-section.

In accordance with the present invention, there is provided an illuminator comprising a device comprising an optical delivery fiber having a core having a first inside diameter joined to a capillary having an outer surface and a capillary tube having an inner surface and a second inside diameter in the region of the joining to the optical delivery fiber, wherein the second inside diameter is less than the first inside diameter of the delivery fiber coupled to a light source. The illuminator can be a PDT illuminator.

In accordance with the present invention, there is provided the use of a device comprising an optical delivery fiber having a core having a first inside diameter joined to a capillary having an outer surface and a capillary tube having an inner surface and a second inside diameter in the region of the joining to the optical delivery fiber, wherein the second inside diameter is less than the first inside diameter of the delivery fiber as a sensor.

DETAILED DESCRIPTION

Figure 1:
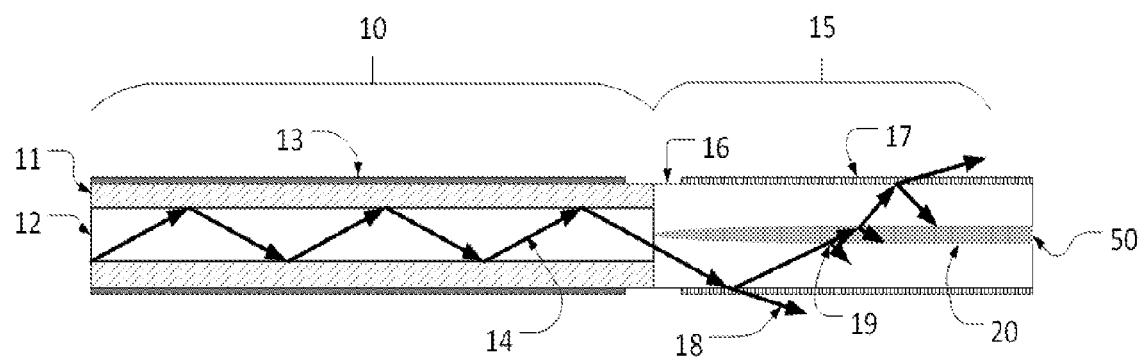
FIG. 1 is a side view of a device where an optical delivery fiber is joined to a collapsed capillary tube.

In the present invention, glass or silica capillaries are used to enhance the diffusion of light delivered by an optical fiber. As opposed to conventional diffusers using coreless optical fibers or bulk scattering elements, here a capillary is introduced to enhance diffusion of the light. This occurs because the capillary tube at the point of coupling to the optical fiber is smaller in diameter than the core of the fiber delivering the light to the capillary. In addition, the capillary can be tapered (i.e. narrowed but not collapsed or totally closed) toward the point where the delivery fiber and capillary fibers can be spliced or otherwise joined together. In effect, the capillary functions to enhance the diffusion of light from a coreless optical fiber.

The profile of the capillary tube can be designed to provide a desired light distribution. In a preferred embodiment, the capillary can be collapsed or totally closed toward the point where the delivery fiber and capillary fibers are spliced together. Other embodiments that vary the capillary tube are described below.

The presence of the capillary introduces a dielectric discontinuity directly into the central portion of an otherwise coreless optical fiber. This results in enhanced scattering, refraction, and reflection. As all of these processes are non-absorptive, the light is efficiently re-directed out of the diffuser. The process can be further enhanced by loading the capillary with scattering particles, and/or liquids with optical index selected to be different from the surrounding material. Light which is coupled into the capillary will propagate with high scattering loss, as the capillary/glass interface is not as smooth as the cladding-glass/core-glass interface of an optical fiber. The inner surface of the capillary can be roughened or textured to enhance the scattering, and the roughening can vary along the capillary to match a pre-determined illumination or scattering pattern.

A key feature of this approach occurs in the region of the splice, where the capillary can be collapsed, or partially collapsed as part of the splicing or joining process. This results in the capillary becoming similar to a coreless, or nearly coreless fiber, which has been shown previously to form a lossy waveguide, in that at the interface of the splice there is efficient coupling of the light from the optic fiber into the capillary. By introducing an additional optical element of the form of the capillary, the loss per unit length is enhanced.

The nearly coreless form of the capillary fiber in the region of the splice results in a high coupling efficiency of light into the diffusing region. By choosing the index of the capillary to be close to that of the delivery fiber, the light is efficiently coupled across the splice interface. Once the light encounters the start of the capillary, light will be reflected and scattered off the dielectric interface, reflected (resulting in higher order modes as the angle of the capillary wall is changing with distance along the capillary), and refracted into (and then out of) the capillary. The capillary forms an annular optical waveguide which has poor propagation properties (large radiative losses) while having low absorptive losses.

As the capillary is not manufactured to telecom optical fiber standards for smoothness, the scattering losses will be high compared to other fiber types at both the inner and outer surfaces of the capillary. By properly choosing the diameter of the capillary, the radiation per unit length can be adjusted. The length over which the capillary is collapsed can also be adjusted. In addition the capillary can be tailored to have a varying diameter along its length, including zero diameter (i.e. creating bubbles in the capillary tube).

The capillary tube can be shaped in a multitude of ways while still falling within the scope of the inventive diffuser, where the inner diameter of the capillary tube is smaller than the inner diameter of the core of the optical delivery fiber. For example, the capillary tube can be flared or widening in diameter in the region of the splice with the optical fiber, as long as the diameter of the capillary tube is smaller than the inner diameter of the core of the optical delivery fiber at the splice.

In the present invention, light from an optical source is coupled into the core of a delivery fiber. A capillary is then attached to the delivery fiber using fusion splicing, or other standard technique. Here one makes use of the lossy, but non-absorptive properties of the capillary fiber to act as a diffuser (e.g. for biological applications). Depending on the optical properties (e.g. scattering) of the capillary/cladding surface, the diffuser can be designed to have the desired radiative properties. These can be uniform light distribution for a desired length, or having a high emissivity over a given length, or multiple sites, as desired. As example techniques, the surface of the cladding or plastic overcoat can be chemically treated, mechanically abraded or sand (or other media) blasted to roughen the surface. Optically resonant structures such as gratings can be etched or otherwise impressed on the surface. The plastic over-coating on the fiber can also acts as a diffuser. Other coatings, with or without scattering particles can be used to coat the fiber in constant or graded thicknesses or densities. Heat-shrink tubing can also be used. The coating can also have indices of refraction chosen for the desired coupling properties. All of the above techniques can graded with length to tailor the emission for a specific application.

The use of a glass capillary allows for low absorption in the diffuser, so high power optical sources as well as small diameter fiber can be used. This is desired for applications like PDT in tumors, where the photo-active agents require high-power, narrow-band CW (Continuous Wave) excitation. The use of glass capillaries also allows the use of shorter wavelengths, in contrast to plastic diffusers which are highly absorbing and can heat when exposed to shorter wavelengths.

In a preferred embodiment, the standard coating is removed from the capillary fiber for splicing and the diffuser is used as is. This approach presents the smallest overall diameter.

In another embodiment, the standard coating is replaced by a coating which is index matched to the material of the capillary fiber and which has scattering particles embedded in the coating. The index-matched coating can be varied in thickness or particle density to achieve the desired distribution. An example of such a coating is heat shrink tubing.

In another embodiment, the coating is abraded or otherwise roughened to tailor the scattering characteristics for a desired application, e.g. to produce a constant intensity as a function of length.

In addition, the capillary can be filled with a scattering or fluorescent material. The material in the capillary can act as an emitter or as a detector, depending on the application. A commercially available example is a ~300 micron outer diameter fiber with a 5 micron capillary tube size.

It is also important to consider the role of the delivery fiber. The delivery fiber is generally Multi-mode in order to efficiently couple to high power laser diode sources. For long propagation distances these modes will tend to average the intensity across the fiber. Even if the input beam intensity distribution is Gaussian at the input, it will emerge as almost uniform (referred to as "flat-top" or "top hat") in intensity.

Standard Multi-Mode (MM) fiber is commercially available in core/cladding (μm) sizes such as 50/125, 62.5/125, 105/125, 200/230, 400/430, 600/630, 1000/1035, etc. In each case coupling of the MM fiber to a capillary fiber allows the capillary fiber to behave as a coupling device (diffuser) to the outside environment.

The length of delivery fiber can also be used to tune the properties of the diffuser. For short lengths of fiber, the intensity distribution will remain approximately Gaussian, so the intensity at the edges of the diffuser will be lower. For longer lengths of delivery fiber, the intensity will be more flat-topped, so the intensity at the edges of the diffuser will be higher.

In the geometry shown in FIG. 1, a capillary is used as a diffuser. Fused silica capillaries are available commercially. The capillary tube introduces an optical interface that will cause scattering, reflection and refraction internally. For a given OD, the diameter of the capillary can be used as an adjustable parameter.

In FIG. 1, an optical fiber 10, consisting of a cladding 11, a core 12, and a coating 13 is spliced or otherwise attached to a capillary 15. The capillary 15 has a coating 17, and contains a inner capillary surface 19 of capillary tube 20.

The coatings 17 are shown to be removed in the region of the joint 16, but may be reapplied, removed completely, or removed and replaced with other coatings or materials such as heat shrink tubing.

Light is conducted along the fiber core 12 by total internal reflection, as shown schematically by arrows 14.

The light from the fiber core 12 is coupled into the capillary glass 16, at the splice with small reflective loss as the indices of the materials are chosen to be similar. Without a core to guide the light in the capillary, light is coupled out at 18, but also scattered, reflected and refracted at 19 due to the dielectric-air interface of the capillary tube 20. The scattering can be modified by filling the capillary tube 20, with material that has an index other than air, and/or by adding scattering particles.

Figure 2:
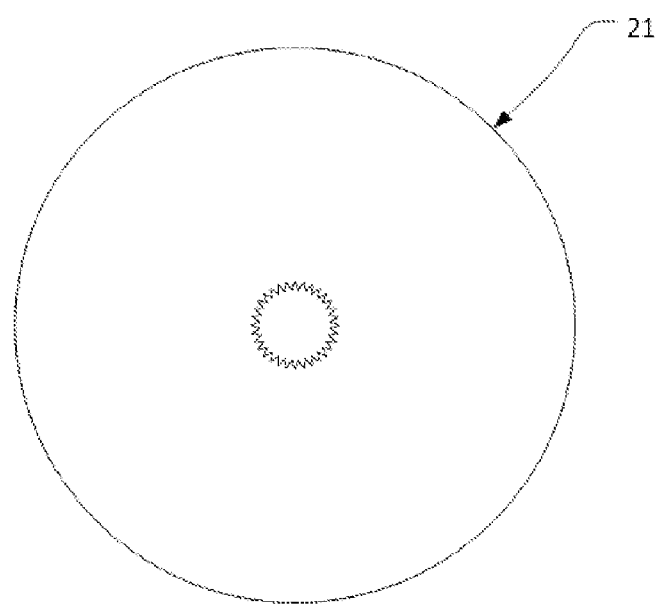
FIG. 2 is a cross section view of a capillary showing a non-circular capillary design.
Figure 3:
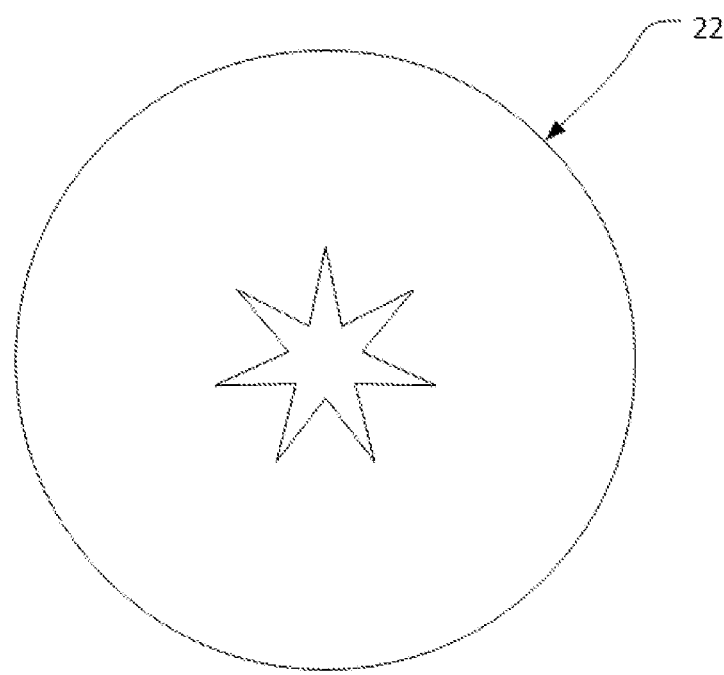
FIG. 3 is a cross section view of a capillary showing a second non-circular capillary design.

FIGS. 2 and 3 show examples of non-circular shapes that can be easily fabricated at the time of the fabrication of the capillary preform. Any deviation that introduces new reflection angles, introduces higher order modes and will increase the coupling of light out of the capillary. Texturing of a given capillary cross section can be further textured to increase scattering.

Note that the capillary can be caused to collapse at the splice, which improves coupling into the silica annulus of the capillary. An example diffuser has been constructed using the following dimensions (dimensions are for all over-coatings removed):

| Delivery Fiber | 300 μm Core | 330 μm Outer Diameter |
|---|---|---|
| Silica Capillary | 5 μm Inner Diameter | 363 μm Outer Diameter |

Figure 4:
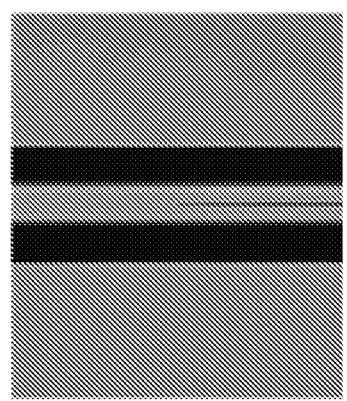
FIG. 4 is a photomicrograph of an optical fiber spliced to a capillary tube where the capillary has been collapsed at the splice.

A photo-micrograph of such a splice is shown in FIG. 4. Note that despite the difference in outer diameter between the fiber and capillary, the outer diameter appears smooth across the splice. Also note that the reduction in outer diameter is accompanied by the complete collapse of the capillary.

Figure 5:
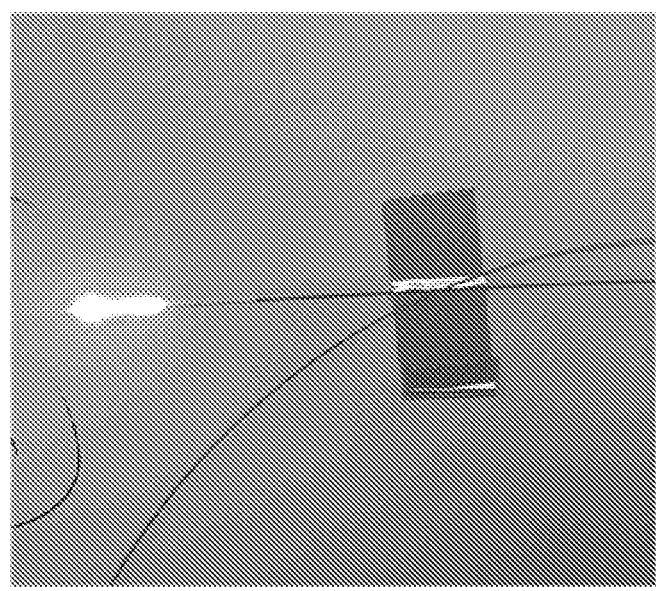
FIG. 5 is a photograph of a 1 cm capillary diffuser illuminated with a 630 nm laser.

A photograph of an example diffuser, 1 cm in length illuminated with a 630 nm laser diode is shown in FIG. 5.

A key feature of this design is that the core diameter of the delivery fiber is greater than the capillary inner diameter.

The distal end labeled 50 in FIG. 1 can be collapsed as well forming a closed capillary which can be used to hold scattering material, or frequency conversion material such as quantum dots. The internal surface of the capillary can be etched to increase scattering, without the mechanical reduction of strength that etching of the outer surface would cause. Collapsing or sealing the distal end of the capillary also allows the diffuser to be more easily sterilized.

In all of the above described implementations, the fiber maintains its inherent flexibility and strength. For insertion into objects such as tumors, standard practice is to use hollow needles and withdraw the needle, leaving the fiber in the tumor.

In another embodiment, the capillary has a plurality of capillary tubes. These plurality of capillary tubes can be used to tailor the diffusive properties of the device or can be filled with a combination of scattering or florescent materials for detecting light from the system, since we note that the diffuser is a linear system, so some of the light incident on the diffuser will be guided back toward the source and can be detected using suitable wavelength separation devices. Light detection can also be done with a single capillary implementation It should be noted that while capillaries are often sold that form an annulus (i.e. are circular in profile and take the shape of a circular prism), capillaries are also sold in other shapes, including rectangular prisms or cubes. These alternative shapes for the capillaries fall within the scope of the invention as long as the capillary tube is smaller than the inner diameter of the core of the optical delivery fiber.

Although the forgoing description and accompanying drawings relate to specific preferred embodiments of the present invention as presently contemplated by the inventor, it will be understood that various changes, modifications and adaptations may be made without departing from the spirit of the invention.

What is claimed is:

1. A device comprising:
   an optical delivery fiber having a core terminating in a core end, the core to transmit light, the core having a first inside diameter; and
   a capillary terminating in a capillary end, the capillary having an outer surface and a capillary tube, the capillary tube having an inner surface, the capillary having a capillary wall disposed between the outer surface and the inner surface;
   wherein:
   the core end is joined and optically coupled to the capillary end to transmit at least some of the light from the core into the capillary wall through the capillary end; and
   the capillary tube has a second inside diameter in the region of the joining to the core end, and the second inside diameter is less than the first inside diameter of the delivery fiber.

2. A device of claim 1 wherein the capillary is a glass or silica capillary.

3. A device of claim 1, wherein the inner surface of the capillary tube is roughened or textured.

4. A device of claim 1, wherein the capillary tube is filled with a material containing optically scattering particles.

5. A device of claim 1, wherein the capillary tube is filled with a material containing fluorescent or other wavelength conversion material.

6. A device of claim 1, wherein the capillary tube is collapsed at two points.

7. A device of claim 1, wherein the capillary tube is tapered in the region of the joining to the optical delivery fiber.

8. A device of claim 1, wherein the capillary tube is collapsed in the region of the joining to the optical delivery fiber.

9. A device of claim 1, wherein the capillary tube is sealed at a distal end of the diffuser.

10. A device of claim 1, further comprising a plurality of capillaries joined to the optical delivery fiber.

11. A device of claim 1, wherein the capillary outer surface is roughened or textured.

12. A device of claim 10, wherein a density of roughening or texturing of the capillary outer surface is varied along the capillary.

13. A device of claim 10, wherein a density of roughening or texturing of the capillary outer surface is varied along the capillary to match a pre-determined light scattering condition.

14. A device of claim 1, wherein the capillary is less than 5 cm long.

15. A device of claim 1, wherein the capillary is approximately 1 cm long.

16. A device of claim 1, wherein the capillary tube has a non-circular cross-section.

17. A device of claim 14, wherein the capillary tube has a star-like cross-section.

18. An illuminator comprising a device of claim 1 coupled to a light source.

19. A method of using the device of claim 1 comprising the steps of coupling a detector to the optical delivery fiber and collecting light in the capillary.

20. The device of claim 7, wherein in the region of the joining to the optical delivery fiber the second inside diameter decreases when moving along a length of the capillary tube towards the capillary end.

* * * * *